US00PP17195P2

(12) United States Plant Patent
Egger

(10) Patent No.: US PP17,195 P2
(45) Date of Patent: Nov. 7, 2006

(54) ***HEUCHERA* PLANT NAMED 'PEACH FLAMBÉ'**

(50) Latin Name: *Heuchera hybrid*
Varietal Denomination: Peach Flambé

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 38 days.

(21) Appl. No.: 11/154,434

(22) Filed: Jun. 15, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
(74) *Attorney, Agent, or Firm*—Klarquist Sparkman, LLP

(57) ABSTRACT

A new and distinct hybrid of *Heuchera* plant characterized by rust to burgundy colored foliage, creamy white flowers on burgundy flowering stems, mounding habit, and excellent vigor.

1 Drawing Sheet

Botanical denomination: *Heuchera* hybrid.
Variety designation: 'Peach Flambé'.
Cross Reference to sibling: *Heuchera* 'Sparkling Burgundy' (U.S. Plant patent application Ser. No. 11/165,707).

The present invention relates to a new and distinct cultivar of *Heuchera* and given the cultivar name of 'Peach Flambé'. *Heuchera* is in the family Saxifragaceae. *Heuchera* 'Peach Flambé' originated from a cross between *Heuchera* H-01-dklf-6 (an unpatented, proprietary plant) as the seed parent, and *Heuchera* 'Amber Waves' (U.S. Plant Pat. No. 13,348) as the pollen parent. Given its ornamental foliage and flower form, it is probable that *Heuchera micrantha, H. americana,* and *H. brizoides* are in its parentage.

This new *Heuchera* is distinguished by:

1. Rust colored spring and summer foliage followed by burgundy winter foliage.
2. Small creamy-white flowers on burgundy peduncles.
3. Mounding habit.
4. Excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The drawing shows a three-year-old plant of *Heuchera* 'Peach Flambé' growing in a five gallon container in the shade house in April in Canby, Oreg.

DETAILED PLANT DESCRIPTION

The following is a detailed description of the new *Heuchera* cultivar based on observations taken in May of a three-year-old specimen grown a five gallon container in an open air shade house with 50% shade cover and added irrigation in the summer months in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart.

Botanical denomination: *Heuchera* hybrid.
Variety designation: 'Peach Flambé'.
Parentage: *Heuchera* H-01-dklf-6 (seed parent, a proprietary, unreleased plant)×*Heuchera* 'Amber Waves' U.S. Plant Pat. No. 13348 (pollen parent).

Plant:
- *Form.*—Basal rosette, herbaceous perennial.
- *Hardiness.*—USDA Zone 4 to 9.
- *Size.*—30 cm tall from the top to the soil to the top of the foliage and 55 cm wide.
- *Habit.*—Mounding.
- *Vigor.*—Excellent.
- *Roots.*—Fibrous, freely branching, fine, and white in color. Roots develop easily from cuttings.

Leaf:
- *Type.*—Simple.
- *Arrangement.*—Rosette.
- *Shape.*—Ovate.
- *Lobing/division.*—5 to 7 main lobes, with 1 to 2 shallow secondary lobes.
- *Venation.*—Palmate.
- *Margins.*—Crenate and slightly undulate.
- *Apex.*—Mucronulate to acute.
- *Base.*—Cordate, lobes sometimes slightly overlapping at the base.
- *Blade size.*—10 cm long and 8 to 8.5 cm wide.
- *Surface texture.*—Sparsely glandular on both sides.
- *Petiole description.*—12 to 21 cm long and 2 mm wide, glandular-pubescent, Red Purple 59B to Greyed Purple 184A.
- *Leaf color.*—Spring, summer topside — Before flowering the new leaves are Greyed Orange 172A to C. Once the flowers open the leaf colors are Greyed Purple 183A on the newest growth to Greyed Orange 172A to Greyed Red 182A on oldest. Bottom side all seasons — Grayed Purple 187C and D. Winter topside — Dark red, Greyed Purple 183A.

Inflorescence:

*Type.*—Thyrse.

*Number of flowers.*—80 per thyrse.

*Number of thyrse in spring.*—12.

*Peduncle.*—60 cm high and 5 mm wide, with glandular hairs, Greyed Purple 187A, with 0 to 3 petiolate cauline leaves (ovate to linear, blades grow to 6 cm long and 4.5 cm wide and are incised at base and crenate).

*Pedicel.*—Variable size, glandular hairs, Grayed Purple 187A.

*Bloom period.*—May in Canby, Oreg.

Flower bud:

*Size.*—2 mm wide and 4 mm long.

*Description.*—Glandular puberulent, ovoid.

*Color.*—Creamy white, Yellow White 158A with tip and base Greyed Orange 174A.

Flower:

*Type.*—Perfect, zygomorphic.

*Shape.*—Campanulate.

*Size.*—6 mm long and 3.5 mm wide.

*Petal description.*—5 in number, extruding from the calyx, 2.5 mm long, spatulate with a clawed base, reflexed, apex acute, margin entire, White 155D on both sides, sparsely glandular on back side only.

*Calyx description.*—5 lobes, divided ⅓ way to the base, with glandular hairs on back side only, apex acute, margin entire, 4.5 mm long and 3 mm wide.

*Calyx and overall flower color.*—Creamy-white, Yellow White 158A to 158B overall with the tips on the outside Greyed Orange 174A and base on the outside Greyed Orange 164B.

*Stamen description.*—5, reduced, sterile, filaments 0.6 mm, White 155B, anthers 0.4 mm long, Green Yellow 1C.

*Pistil description.*—Green Yellow 1C overall, 4 mm long, style 1.5 mm.

*Fragrance.*—None.

*Lastingness.*—Each thyrse blooms for about 2 weeks on the plant.

Fruit:

*Type.*—Two-beaked ovoid capsule.

*Color.*—Brown 200D.

Seed:

*Shape.*—Linear.

*Size.*—2 mm long.

*Color.*—Black, RHS 202A.

Pest and disease tolerance: Excellent disease resistance to powdery mildew, the common problem of *Heuchera*. Susceptible to *Heuchera* rust and root weevils.

COMPARISON TO SIMILAR *HEUCHERAS*

Compared to *Heuchera* 'Amber Waves' (U.S. Plant Pat. No. 13,348), the seed parent, *Heuchera* 'Peach Flambé' has greater vigor. The foliage of this new cultivar is less ruffled, larger, and a deeper orange red color.

Compared to *Heuchera* 'Huntsman', the pollen parent, the new cultivar has peach colored leaves rather than green leaves with grey brown veins, and small creamy white rather than larger salmon pink flowers.

Compared to *Heuchera* 'Marmalade' (U.S. Plant patent application Ser. No. 10/871,960), this cultivar is more compact in habit with leaves that are larger, shinier, less ruffled, and with more orange and red tones.

Compared to *Heuchera* 'Peach Melba' (U.S. Plant patent application Ser. No. 11/153,514), the new variety is more vigorous, with stronger colored leaves of rust to red rather than muted peach tones. The leaves of the new variety are not veiled like *Heuchera* 'Peach Melba'. The flowers of the new variety are white rather than creamy pink.

I claim:

1. A new and distinct hybrid of *Heuchera* plant as herein illustrated and described.

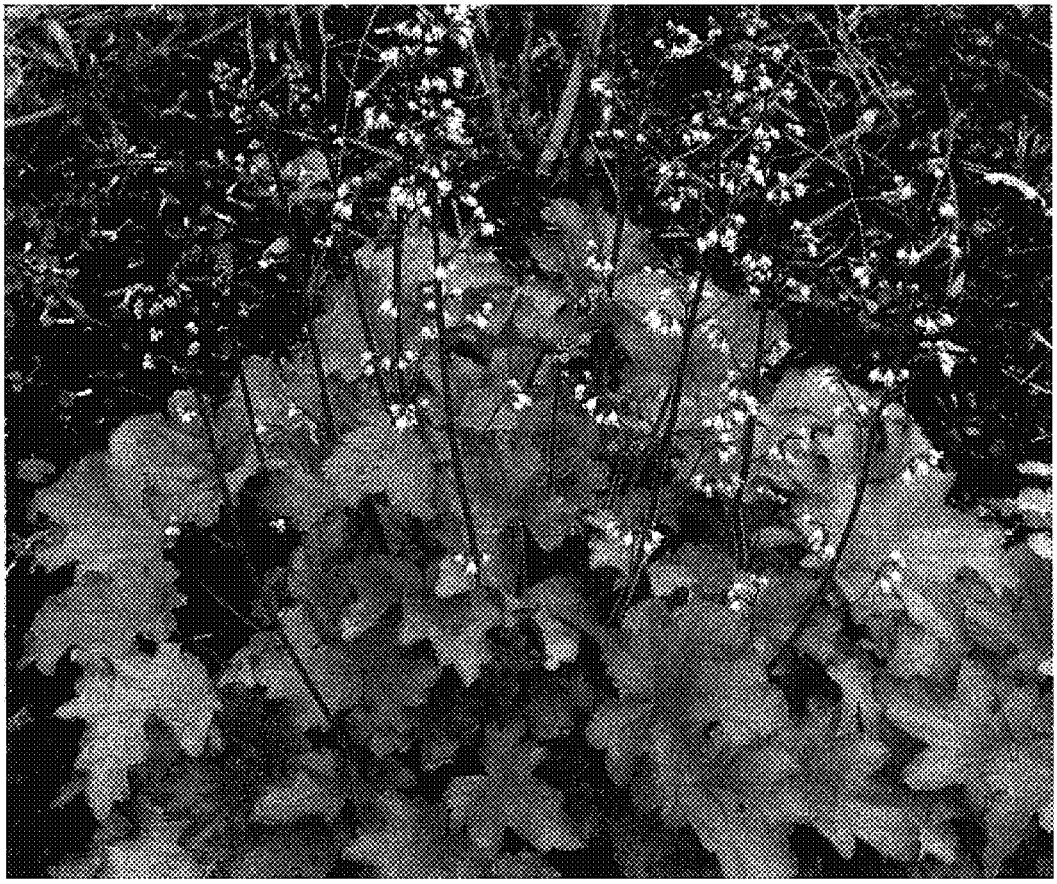

* * * * *